United States Patent [19]

Cardis

[11] Patent Number: 4,744,912

[45] Date of Patent: May 17, 1988

[54] SULFURIZED ANTIWEAR ADDITIVES AND COMPOSITIONS CONTAINING SAME

[75] Inventor: Angeline B. Cardis, Florence, N.J.

[73] Assignee: Mobil Oil Corporation, New York, N.Y.

[21] Appl. No.: 38,084

[22] Filed: Apr. 14, 1987

[51] Int. Cl.⁴ ............... C10M 141/10; C10M 141/08; C10M 141/06
[52] U.S. Cl. .............................. 252/46.7; 252/32.7 R; 558/70; 558/134
[58] Field of Search .................... 252/46.7, 32.7 R; 558/70, 134

[56] References Cited

U.S. PATENT DOCUMENTS

| | | | |
|---|---|---|---|
| 2,833,714 | 5/1958 | Richardson et al. | 252/32.7 R |
| 3,553,131 | 1/1971 | Hepplewhite et al. | 252/46.7 |
| 4,575,431 | 3/1986 | Salentine | 252/46.7 |
| 4,579,666 | 4/1986 | Schroeck | 252/46.7 |

*Primary Examiner*—William R. Dixon, Jr.
*Assistant Examiner*—Jerry D. Johnson
*Attorney, Agent, or Firm*—Alexander J. McKillop; Michael G. Gilman; Howard M. Flournoy

[57] ABSTRACT

Reaction products of sulfurized olefins, e.g., isobutylene with a dialkyl hydrogen phosphite and an alkyl primary amine provide antiwear characteristics and improved retention of copper corrosion protection for lubricant compositions when incorporated therein.

13 Claims, No Drawings

SULFURIZED ANTIWEAR ADDITIVES AND COMPOSITIONS CONTAINING SAME

BACKGROUND OF THE INVENTION

This application is directed to reaction products prepared from sulfurized olefins, dialkyl hydrogen phosphites and primary alkyl amines and lubricant compositions containing same.

Reaction products of sulfurized isobutylene with a dialkyl hydrogen phosphite and an alkyl primary amine offer improved antiwear protection when compared to the sulfurized olefin itself and impart improved retention of copper corrosion protection when blended into fully formulated lubricants.

Sulfurized olefins are commonly added to lubricants to improve load-carrying properties. Esters of phosphorus acids, such as dialkyl hydrogen phosphites, are also added to improve antiwear and oxidative stability. Amino or amine containing reaction products have long been added to lubricants, for example, the reaction product of trithiones with polyamines is highly useful in lubricants as detergents. However, no reference is known to applicant of the reaction product of a sulfurized olefin with a dialkyl hydrogen phosphite and an alkyl primary amine utilized as antiwear lubricant additives.

SUMMARY OF THE INVENTION

This invention is more particularly directed to lubricant compositions comprising a major amount of an oil of lubricating viscosity or grease prepared therefrom and a minor antiwear/anticorrosion amount of the product derived from the reaction of a sulfurized olefin, e.g., isobutylene with a dialkyl hydrogen phosphite and a dialkyl primary amine.

DESCRIPTION OF PREFERRED EMBODIMENTS

Sulfurized olefins useful in the present invention include but are not limited to $C_2$ to about $C_8$ olefins. Preferred are $C_4$ olefins and most particularly preferred is isobutylene. The sulfurized olefins may be prepared by any convenient means known in the art or obtained as articles of commerce. For example, the sulfurized olefins may be prepared in accordance with U.S. Pat. Nos. 3,703,504 or 3,703,505.

The dialkyl hydrogen phosphites have the general formula

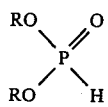

where each R is independently $C_1$ to about $C_{30}$ alkyl. Preferred are $C_1$ to $C_8$, e.g., butyl or isobutyl. This reactant may also be obtained commercially or prepared by any convenient means known in the art.

The amines useful herein have the general formula

where R may be alkyl, aryl, alkaryl, aralkyl, cycloalkyl or substituted moieties thereof having from about 1 to about 30 carbon atoms, when aryl it contains from 6 to about 14 carbon atoms in the aryl group. Preferred are alkyl amines, alkenyl amines such as oleyl amine. Usually the reactants are reacted in a weight ratio of 3.0 to 0.5 to 1.0 to about 7.0 to 1.0 to 1.3 of sulfurized olefin to amine to phosphite at temperatures varying from about 90° to about 130° C. at ambient pressure or higher if desired for times varying from about 2 hours or less up to about 12. The reaction parameters will vary, of course, with the particular reactants, time, temperature and pressure. It should be noted that the reaction temperature is apparently critical for producing effective antiwear/anticorrosion additive products. Note product analysis and particularly the evaluation of Examples 1, 2 and 5.

In general the reaction products of the present invention may be employed in any amount which is effective for imparting the desired degree of antiwear activity. In many applications the products are effectively employed in amounts from about 0.01% to about 20% by weight and preferably from about 0.2% to about 5% of the total weight of the composition. These products may be incorporated into various lubricating media, for example, liquid hydrocarbon oils in the form of either a mineral oil or a synthetic oil, or in the form of a grease, in which any of the aforementioned oils are employed as a vehicle. These lubricants can also contain detergents and dispersants, as well as inhibitors, antiwear, extreme pressure, antifoam, pour depressant, and viscosity index improving additives without negating the beneficial properties of the novel additives/products of this invention.

In general, mineral oils employed as the lubricant or grease vehicle may be of any suitable lubricating viscosity range, for example, from about 45 SSU at 100° F. to about 6,000 SSU at 100° F., and preferably from about 50 SSU at 210° F. to about 250 SSU at 210° F. These oils may have viscosity indexes varying from below 0 to about 100 or higher. Viscosity indexes from about 70 to about 95 are preferred. The average molecular weight of these oils may range from about 250 to 800. Where the lubricant is to be employed in the form of a grease, the lubricating oil is generally employed in an amount sufficient to balance the total grease composition, after accounting for the desired quantity of the thickening agent, and other additive components to be included in the grease formulation.

In instances where synthetic oils are employed as the vehicle for the grease, in preference to mineral oils or in combination therewith, various compounds of this type may be successfully utilized. Typical synthetic vehicles include polyisobutylenes, polybutenes, hydrogenated polydecenes, polypropylene glycol, polyethylene glycol, trimethylol propane esters, neopentyl and pentaerythritol esters, di(2-ethylhexyl)sebacate, di(2-ethylhexyl)adipate, di(butylphthalate)fluorocarbons, silicate esters, silanes, esters of phosphorus-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis(p-phenoxy phenyl)ether, phenoxy phenylethers, etc.

The following examples are merely illustrative of the invention and are not meant to limit it in any way.

EXAMPLE 1

Sulfurized isobutylene (122 g, 46% sulfur) prepared according to the procedure of U.S. Pat. No. 3,703,504, oleylamine (19.5 g, 0.07 moles) commercial product, and dibutyl hydrogen phosphite (22.5 g, 0.11 moles)

were stirred under a nitrogen sweep at 50°–55° C. for four hours. The product was filtered and cooled.

EXAMPLE 2

The same reactants as in Example 1 were reacted at 68°–72° C. for four hours.

EXAMPLE 3

The same reactants as in Example 1 were reacted at 98°–104° C. for four hours.

EXAMPLE 4

The same reactants as in Example 1 were reacted at 118°–122° C. for four hours.

EXAMPLE 5

The same reactants as in Example 1 were reacted at 68°–72° for eight hours.

| | Product Analysis | | | |
|---|---|---|---|---|
| | Increased Infrared Band at* | | | |
| Example | 1212 cm$^{-1}$ | 1060 cm$^{-1}$ | 730 cm$^{-1}$ | 580 cm$^{-1}$ |
| 1 | No | No | No | No |
| 2 | No | No | No | No |
| 3 | Strong | Yes | Slight | Yes |
| 4 | Strong | Yes | Slight | Yes |
| 5 | No | No | No | No |

*No reaction indicated by infrared analysis

EVALUATION OF PRODUCTS

A. The products herein described were blended in mineral oil and tested in the Shell Four-Ball Test. The results in the Table below clearly show that the products of Examples 2, 3 and 4 are effective in protecting metal surfaces from wear.

| Four-Ball Wear Test, 1.5% Additive Concentration Wear Scar Diameter (mm), ½ Inch 52100 Steel Balls, 60 kg, 30 Minutes | | | |
|---|---|---|---|
| | T °C. | 1000 rpm | 2000 rpm |
| Base Stock | 200 | 1.5 | 2.0 |
| | 390 | 1.8 | 1.9 |
| Sulfurized | 200 | 0.7 | 1.3 |
| Olefin of | 390 | 1.6 | 1.4 |
| U.S. 3,703,504 | | | |
| Example 2 | 200 | 0.4 | 0.5 |
| | 390 | 0.75 | 1.65 |
| Example 3 | 200 | 0.4 | 0.5 |
| | 390 | 0.75 | 1.55 |
| Example 4 | 200 | 0.4 | 0.5 |
| | 390 | 0.9 | 1.40 |

Using a modified 4-Ball machine three stationary balls are placed in a lubricant cup and a lubricant containing the additive to be tested is added thereto. A fourth ball is placed on a chuck mounted on a device which can be used to spin the ball at known speeds and loads.

1.5 percent by weight of each product was placed in a blend of a solvent paraffinic bright solvent paraffinic neutral mineral oil. The samples were tested at various temperatures and speeds, but always at a load of 60 Kg and for 30 minutes. The above Table summarizes the test results. The 4-Ball Wear Test is also described in U.S. Pat. No. 4,405,470.

The products of Examples 1 through 4 were blended at 5.0 wt. percent into a fully formulated automotive gear oil and evaluated in ASTM D-130-6 Copper Corrosion test for 3 hours at 121° C. The results clearly demonstrate improved retention of copper corrosion protection for the products of Examples 3 and 4 compared to Examples 1 and 2, where reaction is not indicated by infrared analysis.

| | D-130-6 Rating | | | |
|---|---|---|---|---|
| | Ex. 1 | Ex. 2 | Ex. 3 | Ex. 4 |
| Initial | 2C | 1B | 2C | 3B |
| 4 Weeks at Ambient | 3B | 3B | 2B | 2D |
| 3 Weeks at 55° C. | 3B | 3B | 1B | 1B |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A product of a one-step reaction prepared by reacting a sulfurized olefin with a dialkyl hydrogen phosphite and an alkyl primary amine wherein a $C_2$ to about a $C_8$ sulfurized olefin is reacted with a $C_2$ to about a $C_8$ dialkyl hydrogen phosphite and a $C_2$ to about a $C_{20}$ primary amine in a weight ratio of sulfurized olefin to phosphite to amine of from about 3.0:0.5:1.0 to about 7.0:1.0:1.3 at a temperature of from about 90° C. to about 130° C.

2. The product of claim 1 wherein the sulfurized olefin is sulfurized isobutylene, the hydrogen phosphite is dibutyl hydrogen phosphite and the amine is oleylamine.

3. The product of claim 2 wherein the temperature varies from about 95° to about 105° C.

4. The product of claim 2 wherein the temperature varies from about 115° to about 125° C.

5. An improved lubricant composition comprising a major amout of a lubricant comprising an oil of lubricating viscosity or grease prepared therefrom and a minor antiwear/anticorrosion amount of the one-step reaction product of a sulfurized olefin, a dialkyl hydrogen phosphite and a primary amine wherein said sulfized olefin contains from 2 to 8 carbon atoms said phosphite has from 2 to about 8 carbon atoms and said amine has from about 2 to about 20 carbon atoms and are reacted in a weight ratio of olefin to phosphite to amine of from about 3.0:0.5:1.0 to about 7.0:1.0:1.3 at a temperature of from about 90° C. to about 130° C.

6. The composition of claim 5 wherein the lubricant is a grease.

7. The composition of claim 5 wherein the lubricant is an oil of lubricating viscosity.

8. The composition of claim 7 wherein the lubricant is selected from mineral oils, synthetic oils or mixtures of mineral and synthetic oils.

9. The composition of claim 8 wherein the lubricant is a mineral oil.

10. The composition of claim 8 wherein the lubricant is a synthetic oil.

11. The composition of claim 5 wherein the olefin is sulfurized isobutylene, the phosphite dibutyl hydrogen phosphite and the amine is oleyl amine.

12. The composition of claim 11 wherein the temperature varies from about 95° to about 105° C.

13. The composition of claim 11 wherein the temperature varies from about 115° to about 125° C.

* * * * *